(12) United States Patent
Tyrrell et al.

(10) Patent No.: US 11,935,129 B2
(45) Date of Patent: Mar. 19, 2024

(54) METHODS FOR AUTOMATICALLY DETERMINING INJURY TREATMENT RELATION TO A MOTOR VEHICLE ACCIDENT AND DEVICES THEREOF

(71) Applicant: Mitchell International, Inc., San Diego, CA (US)

(72) Inventors: Norman E. Tyrrell, San Diego, CA (US); Olaf Wied, San Diego, CA (US); Jonathan Navarrete, San Diego, CA (US); Christopher Williamson, Escondido, CA (US); Paul Zaino, Carslbad, CA (US)

(73) Assignee: Mitchell International, Inc., San Diego, CA (US)

( * ) Notice: Subject to any disclaimer, the term of this patent is extended or adjusted under 35 U.S.C. 154(b) by 48 days.

(21) Appl. No.: 17/742,314

(22) Filed: May 11, 2022

(65) Prior Publication Data

US 2022/0270181 A1 Aug. 25, 2022

Related U.S. Application Data

(63) Continuation-in-part of application No. 16/570,758, filed on Sep. 13, 2019, now abandoned.
(Continued)

(51) Int. Cl.
*G06Q 40/08* (2012.01)
*G06T 7/246* (2017.01)
(Continued)

(52) U.S. Cl.
CPC ............ *G06Q 40/08* (2013.01); *G06T 7/246* (2017.01); *G06V 10/761* (2022.01);
(Continued)

(58) Field of Classification Search
None
See application file for complete search history.

(56) References Cited

U.S. PATENT DOCUMENTS

| 6,381,561 B1 * | 4/2002 | Bomar, Jr. ............ G06Q 99/00 702/142 |
| 6,885,981 B2 | 4/2005 | Bomar, Jr. et al. |

(Continued)

OTHER PUBLICATIONS

Nakahara et al., Bridging Classification for injury diagnoses that can be converted to both the International Classification of Diseases and the Abbreviated Injury Scale, Jan. 6, 2014, Acute Medicine & Surgery, vol. 1(1), pp. 1-7 (Year: 2014).*

(Continued)

*Primary Examiner* — Paul S Schwarzenberg
(74) *Attorney, Agent, or Firm* — Sheppard Mullin Richter & Hampton LLP

(57) ABSTRACT

A method for automatically determining injury treatment relation to a motor vehicle accident comprises obtaining a plurality of images of a damaged motor vehicle, vehicle data describing the motor vehicle, occupant data describing an occupant who occupied the motor vehicle during the motor vehicle accident, and injury data from an electronic insurance claim associated with the motor vehicle accident, the injury data specifying an injury to the occupant; determining a delta velocity value for the damaged motor vehicle by applying a first machine learning model to the set of images of the damaged motor vehicle and the vehicle data; determining an injury severity score by applying a second machine learning model to the delta velocity value for the damaged motor vehicle, the vehicle data, and the occupant data; and automatically adjudicating the electronic insurance claim.

14 Claims, 6 Drawing Sheets

Related U.S. Application Data

(60) Provisional application No. 62/731,524, filed on Sep. 14, 2018.

(51) Int. Cl.
*G06V 10/70* (2022.01)
*G06V 10/74* (2022.01)
*G06V 10/94* (2022.01)
*G06V 20/59* (2022.01)
*G16H 50/30* (2018.01)

(52) U.S. Cl.
CPC .......... *G06V 10/768* (2022.01); *G06V 10/945* (2022.01); *G06V 20/597* (2022.01); *G16H 50/30* (2018.01); *G06T 2207/30236* (2013.01)

(56) References Cited

U.S. PATENT DOCUMENTS

| | | | |
|---|---|---|---|
| 10,106,156 B1* | 10/2018 | Nave | B60W 30/0956 |
| 2002/0103622 A1* | 8/2002 | Burge | G06F 19/00 |
| | | | 702/183 |
| 2003/0200123 A1* | 10/2003 | Burge | G06Q 40/08 |
| | | | 705/4 |
| 2005/0060205 A1* | 3/2005 | Woods | G06Q 40/02 |
| | | | 705/4 |
| 2007/0288135 A1* | 12/2007 | Kidd | G01C 11/06 |
| | | | 701/31.4 |
| 2008/0306996 A1* | 12/2008 | McClellan | G06Q 10/06 |
| 2011/0130111 A1* | 6/2011 | Crandall | B60R 21/015 |
| | | | 455/404.1 |
| 2014/0058763 A1* | 2/2014 | Zizzamia | G06Q 40/08 |
| | | | 705/4 |
| 2015/0084757 A1* | 3/2015 | Annibale | G08B 25/016 |
| | | | 340/436 |
| 2017/0221110 A1* | 8/2017 | Sullivan | G06K 9/78 |
| 2018/0285974 A1* | 10/2018 | Bayley | G06Q 40/04 |
| 2020/0090282 A1 | 3/2020 | Tyrell et al. | |

OTHER PUBLICATIONS

Hua, et al., "A Brief Review of Machine Learning and its Application", 2009, Information Engineering Institute Capital Normal University, entire document pertinent (Year: 2009).*

Treleaven, et al., Computational Finance, published in IEEE Computer (vol. 43, Issue: 12, Dec. 2010), entire document pertinent (Year: 2010).*

Treleaven, et al., Computational Finance, published in IEEE Computer (vol. 43, Issue: 12, Dec. 2020), entire document pertinent (Year 2010).

* cited by examiner

Obtain a plurality of images of a damaged motor vehicle involved in a motor vehicle accident, vehicle data describing the motor vehicle, occupant data describing an occupant who occupied the motor vehicle during the motor vehicle accident, and injury data from an electronic insurance claim associated with the motor vehicle accident, the injury data specifying an injury to the occupant.
300

Determine a delta velocity value for the damaged motor vehicle by applying a first machine learning model to the set of images of the damaged motor vehicle and the vehicle data.
302

Determine an injury severity score by applying a second machine learning model to the delta velocity value for the damaged motor vehicle, the vehicle data, and the occupant data.
304

Identify a first set of one or more condition indications based on a correlation of the injury severity score with a stored mapping of condition indications to injury severity scores.
306

Compare one or more of the condition indications in the first set of condition indications to one or more condition indications in a second set of condition indications in the injury data.
308

Generate a likelihood value based on the comparing, the likelihood value indicating a likelihood that the injury to the occupant resulted from the motor vehicle accident.
310

Provide a graphical user interface (GUI) comprising a plurality of display elements, wherein a first one of the display elements represents the generated likelihood value, and wherein a second one of the display elements is operable by a user to select whether the reported injury should be considered in the adjudication of the insurance claim.
312

Receive, via the GUI, a selection regarding whether the reported injury should be considered in the adjudication of the insurance claim.
314

Automatically adjudicate the electronic insurance claim based on the generated likelihood value.
316

FIG. 3

METHODS FOR AUTOMATICALLY DETERMINING INJURY TREATMENT RELATION TO A MOTOR VEHICLE ACCIDENT AND DEVICES THEREOF

CROSS REFERENCE TO RELATED APPLICATIONS

The present application is a continuation-in-part of U.S. patent application Ser. No. 16/570,758, filed Sep. 13, 2019, entitled "METHODS FOR AUTOMATICALLY DETERMINING INJURY TREATMENT RELATION TO A MOTOR VEHICLE ACCIDENT AND DEVICES THEREOF," which claims priority to U.S. Provisional Patent Application No. 62/731,524, filed Sep. 14, 2018, entitled "METHODS FOR AUTOMATICALLY DETERMINING INJURY TREATMENT RELATION TO A MOTOR VEHICLE ACCIDENT AND DEVICES THEREOF," the disclosures thereof incorporated by reference herein in their entirety.

DESCRIPTION OF RELATED ART

The disclosed technology relates to methods, non-transitory computer readable media, and devices for automated data and image analysis to determine injury treatment relation to a motor vehicle accident.

SUMMARY

In general, one aspect disclosed features a method for automatically determining injury treatment relation to a motor vehicle accident, the method comprising: obtaining, by an insurance claim analysis device, a plurality of images of a damaged motor vehicle involved in a motor vehicle accident, vehicle data describing the motor vehicle, occupant data describing an occupant who occupied the motor vehicle during the motor vehicle accident, and injury data from an electronic insurance claim associated with the motor vehicle accident, the injury data specifying an injury to the occupant; determining, by the insurance claim analysis device, a delta velocity value for the damaged motor vehicle by applying a first machine learning model to the set of images of the damaged motor vehicle and the vehicle data; determining, by the insurance claim analysis device, an injury severity score by applying a second machine learning model to the delta velocity value for the damaged motor vehicle, the vehicle data, and the occupant data; identifying, by the insurance claim analysis device, a first set of one or more condition indications based on a correlation of the injury severity score with a stored mapping of condition indications to injury severity scores; comparing, by the insurance claim analysis device, one or more of the condition indications in the first set of condition indications to one or more condition indications in a second set of condition indications in the injury data; generating, by the insurance claim analysis device, a likelihood value based on the comparing, the likelihood value indicating a likelihood that the injury to the occupant resulted from the motor vehicle accident; and automatically adjudicating, by the insurance claim analysis device, the electronic insurance claim based on the generated likelihood value.

Embodiments of the method may include one or more of the following features. Some embodiments comprise providing, by the insurance claim analysis device, a graphical user interface (GUI) comprising a plurality of display elements, wherein a first one of the display elements represents the generated likelihood value, and wherein a second one of the display elements is operable by a user to select whether the reported injury should be considered in the adjudication of the insurance claim; and receiving, by the insurance claim analysis device and via the GUI, a selection regarding whether the reported injury should be considered in the adjudication of the insurance claim. Some embodiments comprise obtaining, by the insurance claim analysis device, further injury data from a medical bill of the occupant; comparing, by the insurance claim analysis device, one or more of the condition indications in the first set of condition indications to one or more condition indications in a second set of condition indications in the injury data and one or more condition indications in a third set of condition indications in the further injury data; generating, by the insurance claim analysis device, a further likelihood value based on the comparing, the further likelihood value indicating a further likelihood that the injury to the occupant resulted from the motor vehicle accident; and automatically adjudicating, by the insurance claim analysis device, the electronic insurance claim based on the generated further likelihood value. In some embodiments, the condition indications comprise International Statistical Classification of Diseases and Related Health Problems (ICD) codes and the injury severity score comprises an Abbreviated Injury Scale (AIS) score. Some embodiments comprise applying, by the insurance claim analysis device, one or more machine learning models to automatically generate the injury severity score or automatically analyze obtained images of the damaged motor vehicle to generate the delta velocity value. In some embodiments, the vehicle data comprises one or more of a type of the motor vehicle, an age of the motor vehicle, a size of the motor vehicle, a weight of the motor vehicle, an area of impact on the motor vehicle, a damage extent, one or more crush measurements, or whether the motor vehicle was drivable subsequent to the motor vehicle accident. In some embodiments, the occupant data comprises one or more of demographic data regarding the occupant comprising one or more of an occupant age, weight, height, or gender, where the occupant was sitting in the motor vehicle, a point of impact on the motor vehicle, or whether an airbag deployed as a result of the motor vehicle accident.

In general, one aspect disclosed features an insurance claim analysis device comprising memory comprising programmed instructions stored thereon and one or more processors configured to execute the stored programmed instructions to preform a method comprising: obtaining, by an insurance claim analysis device, a plurality of images of a damaged motor vehicle involved in a motor vehicle accident, vehicle data describing the motor vehicle, occupant data describing an occupant who occupied the motor vehicle during the motor vehicle accident, and injury data from an electronic insurance claim associated with the motor vehicle accident, the injury data specifying an injury to the occupant; determining, by the insurance claim analysis device, a delta velocity value for the damaged motor vehicle by applying a first machine learning model to the set of images of the damaged motor vehicle and the vehicle data; determining, by the insurance claim analysis device, an injury severity score by applying a second machine learning model to the delta velocity value for the damaged motor vehicle, the vehicle data, and the occupant data; identifying, by the insurance claim analysis device, a first set of one or more condition indications based on a correlation of the injury severity score with a stored mapping of condition indications to injury severity scores; comparing, by the insurance claim analysis device, one or more of the condition indications in the first set of condition indications to one or more condition indications in a second set of condition indications in the injury data; generating, by the insurance claim analysis device, a likelihood value based on the comparing, the likelihood value indicating a likelihood that the injury to the occupant resulted from the motor vehicle accident; and automatically adjudicating, by the insurance claim analysis device, the electronic insurance claim based on the generated likelihood value.

Embodiments of the device may include one or more of the following features. In some embodiments, the method further comprises: providing, by the insurance claim analysis device, a graphical user interface (GUI) comprising a plurality of display elements, wherein a first one of the display elements represents the generated likelihood value, and wherein a second one of the display elements is operable by a user to select whether the reported injury should be considered in the adjudication of the insurance claim; and receiving, by the insurance claim analysis device and via the GUI, a selection regarding whether the reported injury should be considered in the adjudication of the insurance claim. In some embodiments, the method further comprises: obtaining, by the insurance claim analysis device, further injury data from a medical bill of the occupant; comparing, by the insurance claim analysis device, one or more of the condition indications in the first set of condition indications to one or more condition indications in a second set of condition indications in the injury data and one or more condition indications in a third set of condition indications in the further injury data; generating, by the insurance claim analysis device, a further likelihood value based on the comparing, the further likelihood value indicating a further likelihood that the injury to the occupant resulted from the motor vehicle accident; and automatically adjudicating, by the insurance claim analysis device, the electronic insurance claim based on the generated further likelihood value. In some embodiments, the condition indications comprise International Statistical Classification of Diseases and Related Health Problems (ICD) codes and the injury severity score comprises an Abbreviated Injury Scale (AIS) score. In some embodiments, the method further comprises: applying, by the insurance claim analysis device, one or more machine learning models to automatically generate the injury severity score or automatically analyze obtained images of the damaged motor vehicle to generate the delta velocity value. In some embodiments, the vehicle data comprises one or more of a type of the motor vehicle, an age of the motor vehicle, a size of the motor vehicle, a weight of the motor vehicle, an area of impact on the motor vehicle, a damage extent, one or more crush measurements, or whether the motor vehicle was drivable subsequent to the motor vehicle accident. In some embodiments, the occupant data comprises one or more of demographic data regarding the occupant comprising one or more of an occupant age, weight, height, or gender, where the occupant was sitting in the motor vehicle, a point of impact on the motor vehicle, or whether an airbag deployed as a result of the motor vehicle accident.

In general, one aspect disclosed features a non-transitory machine readable medium having stored thereon instructions for automatically determining injury treatment relation to a motor vehicle accident comprising executable code that, when executed by one or more processors, causes the processors to perform a method comprising: obtaining, by an insurance claim analysis device, a plurality of images of a damaged motor vehicle involved in a motor vehicle accident, vehicle data describing the motor vehicle, occupant data describing an occupant who occupied the motor vehicle during the motor vehicle accident, and injury data from an electronic insurance claim associated with the motor vehicle accident, the injury data specifying an injury to the occupant; determining, by the insurance claim analysis device, a delta velocity value for the damaged motor vehicle by applying a first machine learning model to the set of images of the damaged motor vehicle and the vehicle data; determining, by the insurance claim analysis device, an injury severity score by applying a second machine learning model to the delta velocity value for the damaged motor vehicle, the vehicle data, and the occupant data; identifying, by the insurance claim analysis device, a first set of one or more condition indications based on a correlation of the injury severity score with a stored mapping of condition indications to injury severity scores; comparing, by the insurance claim analysis device, one or more of the condition indications in the first set of condition indications to one or more condition indications in a second set of condition indications in the injury data; generating, by the insurance claim analysis device, a likelihood value based on the comparing, the likelihood value indicating a likelihood that the injury to the occupant resulted from the motor vehicle accident; and automatically adjudicating, by the insurance claim analysis device, the electronic insurance claim based on the generated likelihood value.

Embodiments of the medium may include one or more of the following features. In some embodiments, the method further comprises: providing, by the insurance claim analysis device, a graphical user interface (GUI) comprising a plurality of display elements, wherein a first one of the display elements represents the generated likelihood value, and wherein a second one of the display elements is operable by a user to select whether the reported injury should be considered in the adjudication of the insurance claim; and receiving, by the insurance claim analysis device and via the GUI, a selection regarding whether the reported injury should be considered in the adjudication of the insurance claim. In some embodiments, the method further comprises: obtaining, by the insurance claim analysis device, further injury data from a medical bill of the occupant; comparing, by the insurance claim analysis device, one or more of the condition indications in the first set of condition indications to one or more condition indications in a second set of condition indications in the injury data and one or more condition indications in a third set of condition indications in the further injury data; generating, by the insurance claim analysis device, a further likelihood value based on the comparing, the further likelihood value indicating a further likelihood that the injury to the occupant resulted from the motor vehicle accident; and automatically adjudicating, by the insurance claim analysis device, the electronic insurance claim based on the generated further likelihood value. In some embodiments, the condition indications comprise International Statistical Classification of Diseases and Related Health Problems (ICD) codes and the injury severity score comprises an Abbreviated Injury Scale (AIS) score. In some embodiments, the method further comprising: applying, by the insurance claim analysis device, one or more machine learning models to automatically generate the injury severity score or automatically analyze obtained images of the damaged motor vehicle to generate the delta velocity value. In some embodiments, the vehicle data comprises one or more of a type of the motor vehicle, an age of the motor vehicle, a size of the motor vehicle, a weight of the motor vehicle, an area of impact on the motor vehicle, a damage extent, one or more crush measurements, or whether the motor vehicle was drivable subsequent to the motor vehicle accident; and the occupant data comprises one or more of demographic data regarding the occupant comprising one or more of an occupant age, weight, height, or gender, where the occupant was sitting in the motor vehicle, a point of impact on the motor vehicle, or whether an airbag deployed as a result of the motor vehicle accident.

The disclosed technology has a number of associated advantages including providing methods, non-transitory computer readable media, and insurance claim analysis devices that facilitate improved accuracy, consistency, and efficiency with respect to analyzing images and data associated with insurance claims to automatically recommend inclusion or exclusion of associated reported injuries from claim adjudication consideration. This technology advantageously utilizes machine learning models to automatically analyze damaged motor vehicle images and other insurance claim data in order to generate and utilize delta velocity values and injury severity scores. The injury severity scores are advantageously mapped to condition indications in order to facilitate an improved, automated determination regarding whether an injury reported as part of an insurance claim likely resulted from an associated motor vehicle accident.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIG. 3 is a flowchart of an exemplary method for automatically determining injury treatment relation to a motor vehicle accident.

The figures are not exhaustive and do not limit the present disclosure to the precise form disclosed.

DETAILED DESCRIPTION

Figure 1:
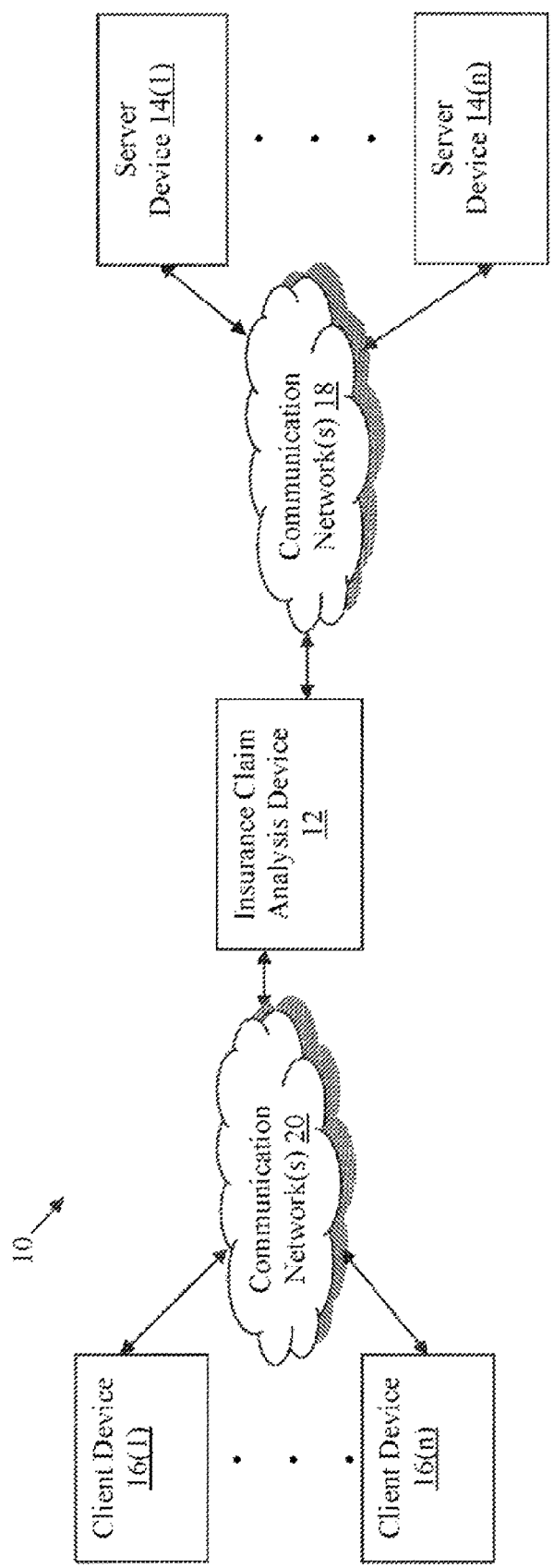
FIG. 1 a block diagram of a network environment with an exemplary insurance claim analysis device.

Referring to FIG. 1, an exemplary network environment 10 with an exemplary insurance claim analysis device 12 is illustrated. The insurance claim analysis device 12 in this example is coupled to a plurality of server devices 14(1)-14(n) and a plurality of client devices 16(1)-16(n) via communication network(s) 18 and 20, respectively, although the insurance claim analysis device 12, server devices 14(1)-14(n), and/or client devices 16(1)-16(n), may be coupled together via other topologies. Additionally, the network environment 10 may include other network devices such as one or more routers and/or switches, for example, which are well known in the art and thus will not be described herein. This technology provides a number of advantages including methods, non-transitory computer readable media, and insurance claim analysis devices that use machine learning models, an automated analysis of image(s) of the damaged motor vehicle, and determination of a delta velocity value and injury severity score for the practical application of determining a likelihood that a reported injury of an occupant of a motor vehicle resulted from an accident involving the motor vehicle during the automated processing of insurance claims.

Figure 2:
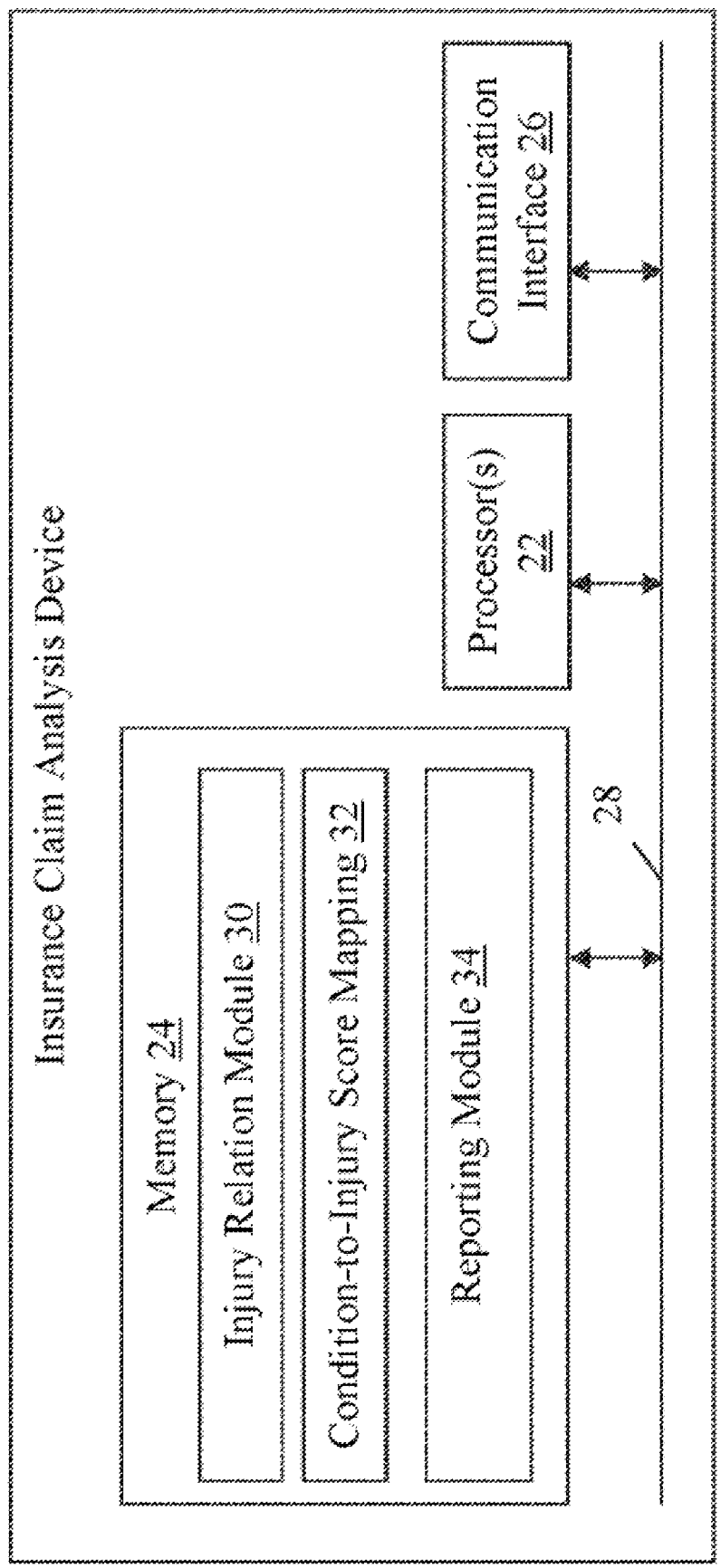
FIG. 2 is a block diagram of the exemplary insurance claim analysis device of FIG. 1.

Referring to FIGS. 1-2, the insurance claim analysis device 12 in this example includes processor(s) 22, a memory 24, and/or a communication interface 26, which are coupled together by a bus 28 or other communication link, although the insurance claim analysis device can include other types and/or numbers of elements in other configurations. The processor(s) 22 of the insurance claim analysis device 12 may execute programmed instructions stored in the memory 24 for the any number of the functions described and illustrated herein. The processor(s) 22 may include one or more CPUs or general purpose processors with one or more processing cores, for example, although other types of processor(s) can also be used.

The memory 24 of the insurance claim analysis device 12 stores these programmed instructions for one or more aspects of the present technology as described and illustrated herein, although some or all of the programmed instructions could be stored elsewhere. A variety of different types of memory storage devices, such as random access memory (RAM), read only memory (ROM), hard disk, solid state drives, flash memory, or other computer readable medium which is read from and written to by a magnetic, optical, or other reading and writing system that is coupled to the processor(s) 22, can be used for the memory 24.

Figure 4:
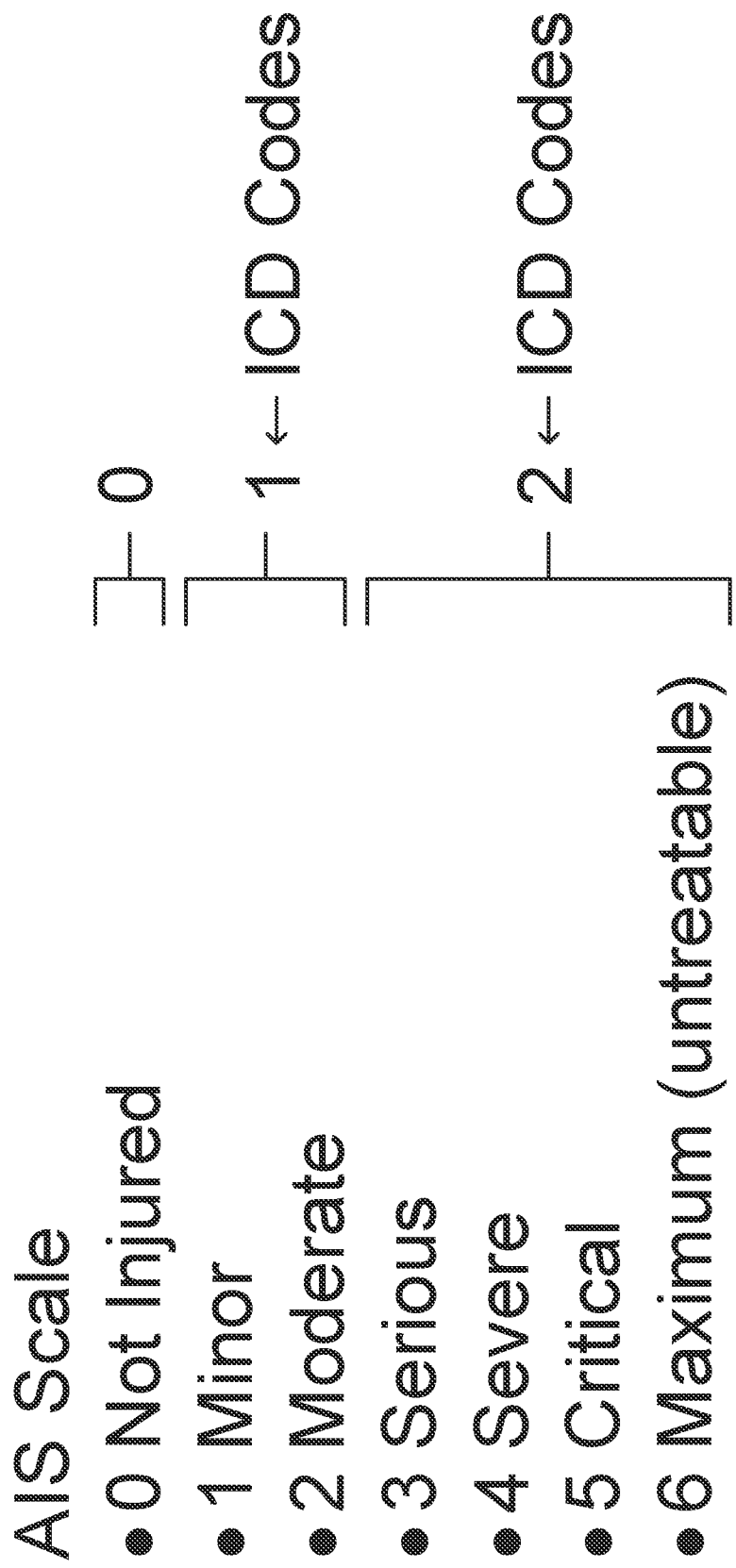
FIG. 4 is an exemplary mapping of condition indications to injury severity scores.
Figure 5:
FIG. 5 is a screenshot of an exemplary graphical user interface (GUI) that can be used to report injury treatment relation to a motor vehicle accident.

Accordingly, the memory 24 can store application(s) that can include executable instructions that, when executed by the insurance claim analysis device 12, cause the insurance claim analysis device 12 to perform actions, such as to transmit, receive, or otherwise process network messages, for example, and to perform other actions described and illustrated below with reference to FIGS. 3-5. The application(s) can be implemented as modules or components of other application(s). Further, the application(s) can be implemented as operating system extensions, module, plugins, or the like.

Even further, the application(s) may be operative in a cloud-based computing environment. The application(s) can be executed within or as virtual machine(s) or virtual server(s) that may be managed in a cloud-based computing environment. Also, the application(s), and even the insurance claim analysis device 12 itself, may be located in virtual server(s) running in a cloud-based computing environment rather than being tied to one or more specific physical network computing devices. Also, the application(s) may be running in one or more virtual machines (VMs) executing on the insurance claim analysis device 12. Additionally, in one or more embodiments of this technology, virtual machine(s) running on the insurance claim analysis device 12 may be managed or supervised by a hypervisor.

In this particular example, the memory 24 includes an injury relation module 30, a condition-to-injury score mapping 32, and a reporting module 34, although the memory 24 can include other policies, modules, databases, or applications, for example. The injury relation module 30 in this example is configured to ingest images of a damaged motor vehicle, vehicle data, occupant data, and injury data. Based on the ingested images and vehicle data, the injury relation module 30 is configured to apply a first machine learning model to automatically determine a delta velocity value associated with an accident involving the damaged motor vehicle. The injury relation module 30 is further configured to apply a second machine learning model to generate an injury severity score based on the delta velocity value, the vehicle data, and the occupant data.

Any machine learning models may be used. For example, the machine learning models and techniques may include classifiers, decision trees, neural networks, gradient boosting, and similar machine learning models and techniques. The machine learning models may be trained previously according to historical correspondences between examples of the inputs and outputs. The training may be supervised, unsupervised, or a combination thereof, and may continue between operations for the lifetime of the system. Outputs of the models may be used to train the models again, for example to improve their accuracy.

With the resulting injury severity score, the injury relation module 30 in this example utilizes the condition-to-injury score mapping 32 to identify condition indications, and determines whether the condition indications correspond with condition indications in the ingested injury data. In one example, the condition-to-injury score mapping 32 includes a mapping of condition indications in the form of International Statistical Classification of Diseases and Related Health Problems (ICD) codes to injury scores in the form of Abbreviated Injury Scale (AIS) scores, although other types of condition indication and/or injury severity scores can also be used in other examples.

The injury data can be reported as part of, or extracted from, a claimant report of injury, an electronic insurance claim, a medical bill, a medical record, or similar documents. Accordingly, the injury relation module 30 can automatically determine, from images of a damaged motor vehicle, a likelihood that reported injuries of an occupant of the damaged motor vehicle resulted from the motor vehicle accident that is associated with an insurance claim in which the injuries were reported. The operation of the injury relation module 30 is described and illustrated in more detail later with reference to FIG. 3.

The reporting module 34 in this example is configured to output at least an indication of the likelihood generated by the injury relation module 30 to the client devices 16(1)-16(n). In one example, the reporting module 34 can generate a graphical user interface (GUI) that includes the indication of the likelihood. In another example, the indication of the likelihood can be provided to a third party or end user GUI or device in response a call received via a provided application programming interface (API), for example. Accordingly, the likelihood can be output by the claim analysis device 12 via a provided GUI or via API consumption, and the likelihood can also be provided via other manners in other examples.

The reporting module 34 in this particular example is further configured to store a selection received from the client devices 16(1)-16(n) regarding whether a reported injury should be considered in an adjudication process associated with an insurance claim. Accordingly, the output likelihood in this example can inform the decision by an insurance adjuster or other automated system, for example, as to whether a reported injury should be considered or was actually a result of a motor vehicle accident associated with an insurance claim.

The communication interface 26 of the insurance claim analysis device 12 operatively couples and communicates between the insurance claim analysis device 12, the server devices 14(1)-14(n), and/or the client devices 16(1)-16(n), which are all coupled together by the communication network(s) 16 and 18, although other types and/or numbers of communication networks or systems with other types and/or numbers of connections and/or configurations to other devices and/or elements can also be used.

By way of example only, the communication network(s) 16 and 18 can include local area network(s) (LAN(s)) or wide area network(s) (WAN(s)), and can use TCP/IP over Ethernet and industry-standard protocols, although other types and/or numbers of protocols and/or communication networks can be used. The communication network(s) 16 and 18 in this example can employ any suitable interface mechanisms and network communication technologies including, for example, teletraffic in any suitable form (e.g., voice, modem, and the like), Public Switched Telephone Network (PSTNs), Ethernet-based Packet Data Networks (PDNs), combinations thereof, and the like.

The insurance claim analysis device 12 can be a stand-alone device or integrated with one or more other devices or apparatuses, such as one or more of the server devices 14(1)-14(n), for example. In one particular example, the insurance claim analysis device 12 can include or be hosted by one of the server devices 14(1)-14(n), and other arrangements are also possible.

Each of the server devices 14(1)-14(n) in this example includes processor(s), a memory, and a communication interface, which are coupled together by a bus or other communication link, although other numbers and/or types of network devices could be used. The server devices 14(1)-14(n) in this example host content associated with insurance carrier(s) including insurance claim data that can include images of damaged motor vehicle, vehicle data, occupant data, and/or injury data, for example.

Although the server devices 14(1)-14(n) are illustrated as single devices, one or more actions of the server devices 14(1)-14(n) may be distributed across one or more distinct network computing devices that together comprise one or more of the server devices 14(1)-14(n). Moreover, the server devices 14(1)-14(n) are not limited to a particular configuration. Thus, the server devices 14(1)-14(n) may contain a plurality of network devices that operate using a master/slave approach, whereby one of the network devices of the server devices 14(1)-14(n) operate to manage and/or otherwise coordinate operations of the other network devices.

The server devices 14(1)-14(n) may operate as a plurality of network devices within a cluster architecture, a peer-to peer architecture, virtual machines, or within a cloud architecture, for example. Thus, the technology disclosed herein is not to be construed as being limited to a single environment and other configurations and architectures are also envisaged.

The client devices 16(1)-16(n) in this example include any type of computing device that can interface with the insurance claim analysis device to submit data and/or receive GUI(s). Each of the client devices 16(1)-16(n) in this example includes a processor, a memory, and a communication interface, which are coupled together by a bus or other communication link, although other numbers and/or types of network devices could be used.

The client devices 16(1)-16(n) may run interface applications, such as standard web browsers or standalone client applications, which may provide an interface to communicate with the insurance claim analysis device 12 via the communication network(s) 20. The client devices 16(1)-16(n) may further include a display device, such as a display screen or touchscreen, and/or an input device, such as a keyboard, for example. In one example, the client devices 16(1)-16(n) can be utilized by insurance adjusters to facilitate an improved analysis of insurance claims as described and illustrated herein, although other types of client devices 16(1)-16(n) utilized by other types of users can also be used in other examples.

Although the exemplary network environment 10 with the insurance claim analysis device 12, server devices 14(1)-14(n), client devices 16(1)-16(n), and communication network(s) 16 and 18 are described and illustrated herein, other types and/or numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

One or more of the devices depicted in the network environment 10, such as the insurance claim analysis device 12, client devices 16(1)-16(n), or server devices 14(1)-14(n), for example, may be configured to operate as virtual instances on the same physical machine. In other words, one or more of the insurance claim analysis device 12, client devices 16(1)-16(n), or server devices 14(1)-14(n) may operate on the same physical device rather than as separate devices communicating through communication network(s) 16 and 18. Additionally, there may be more or fewer insurance claim analysis devices, client devices, or server devices than illustrated in FIG. 1.

In addition, two or more computing systems or devices can be substituted for any one of the systems or devices in any example. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only wireless networks, cellular networks, PDNs, the Internet, intranets, and combinations thereof.

The examples may also be embodied as one or more non-transitory computer readable media, such as the memory 24, having instructions stored thereon for one or more aspects of the present technology as described and illustrated by way of the examples herein. The instructions in some examples include executable code that, when executed by one or more processors, such as the processor(s) 22, cause the processors to carry out steps necessary to implement the methods of the examples of this technology that are described and illustrated herein.

An exemplary method of automatically determining injury treatment relation to a motor vehicle accident will now be described with reference to FIGS. 3-5. The elements of the method are presented in one arrangement. However, it should be understood that one or more elements of the method may be performed in a different order, in parallel, omitted entirely, and the like. Furthermore, the method may include other elements in addition to those presented. For example, the method may include error-handling functions if exceptions occur, and the like.

Referring more specifically to FIG. 3, a flowchart of an exemplary method of automatically determining injury treatment relation to a motor vehicle accident is illustrated. In step 300 in this example, the insurance claim analysis device 12 obtains a plurality of images of a damaged motor vehicle involved in a motor vehicle accident, vehicle data describing the motor vehicle, occupant data describing an occupant who occupied the motor vehicle during the motor vehicle accident, and injury data from an electronic insurance claim or initial report of injury associated with the motor vehicle accident, the injury data specifying an injury to the occupant. The ingested images and data can be obtained from one or more of the server devices 14(1)-14(n) and/or one of the client devices 16(1)-16(n), for example, and can be associated with an insurance claim associated with an accident involving the damaged motor vehicle that was submitted to an insurance carrier. Accordingly, the occupant can be a claimant in some examples.

The vehicle data can include a type of the damaged motor vehicle, an age of the damaged motor vehicle, a size of the damaged motor vehicle, a weight of the damaged motor vehicle, an area of impact on the damaged motor vehicle, a damage extent, one or more crush measurements, stiffness coefficients, which may be obtained from industry data, or whether the damaged motor vehicle was drivable subsequent to the motor vehicle accident, for example, although other types of vehicle data can be used in other examples. In some examples, the occupant data includes demographic data regarding the occupant, such as an occupant age, weight, height, or gender, where the occupant was sitting in the damaged motor vehicle, a point of impact on the damaged motor vehicle, or whether an airbag deployed as a result of the associated motor vehicle accident, for example, although other types of occupant data can also be used in other examples. The injury data can include condition indication(s) (e.g., ICD code(s)) associated with an injury or treatment reported as part of an insurance claim and/or medical bill and/or report of injury associated with the motor vehicle accident, for example.

In step 302, the insurance claim analysis device 12 may determine a delta velocity value for the damaged motor vehicle by applying a first machine learning model to the set of images of the damaged motor vehicle and the vehicle data. The first machine learning model may be trained using historical sets of images and vehicle data along with the delta velocity values obtained from the corresponding historical sets. In order to generate the delta velocity value, the insurance claim analysis device 12 automatically analyzes the obtained images of the damaged motor vehicle and applies a machine learning model based on the analysis and at least a portion of the obtained vehicle data. In one example, the delta velocity can be generated as described and illustrated in more detail in U.S. Provisional Patent Application Ser. No. 62/731,259, filed on Sep. 14, 2018, and entitled "Methods for Improved Delta Velocity Prediction Using Machine Learning and Devices Thereof," which is incorporated herein by reference in its entirety, although other methods of obtaining or generating the delta velocity value can also be used in other examples.

In step 304, the insurance claim analysis device 12 may determine an injury severity score by applying a second machine learning model to the delta velocity value for the damaged motor vehicle, the vehicle data, and the occupant data. The second machine learning model may be trained using historical sets of delta velocity values, vehicle data, and occupant data. along with the injury severity scores obtained from the corresponding historical sets. The injury severity score may be, e.g., an AIS score. The insurance claim analysis device 12 can utilize data regarding where the occupant was sitting in the damaged motor vehicle, occupant demographic data, the area of impact on the damaged motor vehicle, and whether the car was drivable, among other factors and data, for example, to generate the injury severity score.

The machine learning model can optionally be trained using data obtained from the National Automotive Sampling System (NASS) hosted by the National Highway Traffic Safety Administration (NHTSA), and can optionally be updated based on manual feedback or implicit learning, for example, although other methods for training and/or maintaining the second machine learning model can also be used in other examples. It is not well-understood, routine or convention activity in the art to correlate the delta velocity value to an injury severity score via the application of a machine learning model, which improves the accuracy and efficiency of the overall insurance claim processing with respect to the relationship of the reported injury treatments.

In step 306, the insurance claim analysis device 12 may identify a first set of one or more condition indications based on a correlation of the injury severity score with a stored mapping of condition indications to injury severity scores. For example, the mapping may be the stored condition-to-injury score mapping 32. Referring more specifically to FIG. 4, an exemplary mapping of condition indications to injury severity scores is illustrated. In this example, the condition-to-injury score mapping 30 includes AIS scores mapped to ICD codes that correspond with medical treatments, although other types of condition indications or injury severity scores can also be used in other examples.

The AIS scores of 1 and 2 in this example are mapped to a set of ICD codes and the AIS scores of 3-6 are mapped to another set of ICD codes, although any number of AIS scores could be mapped to any number of ICD codes in other examples. Utilizing the stored condition-to-injury score mapping 30 to identify particular condition indications that correlate with a particular injury severity score provides a practical application of facilitating more effective and automated determinations regarding the relation of an injury treatment to a motor vehicle accident, and is not well-understood, routine, or conventional in the art.

Referring back to FIG. 3, in step 308, the insurance claim analysis device 12 may compare one or more of the condition indications in the first set of condition indications to one or more condition indications in a second set of condition indications in the injury data. For example, the insurance claim analysis device 12 may determine whether the condition indication(s) in the injury data obtained in step 300 match condition indication(s) in the set of condition indications identified in step 306. The conditions indication(s) in the injury data can correspond with medical treatments of the occupant of the damaged motor vehicle that were reported on an associated insurance claim, for example.

Accordingly, the insurance claim analysis device 12 compares the condition indication(s) in the injury data to the identified set of condition indications that correspond with a generated injury severity score to determine whether the condition indication(s) are associated with a reported injury that likely resulted from the motor vehicle accident.

In step 310, the insurance claim analysis device 12 may generate a likelihood value based on the comparing, the likelihood value indicating a likelihood that the injury to the occupant resulted from the motor vehicle accident.

In step 312, the insurance claim analysis device 12 may provide a graphical user interface (GUI) comprising a plurality of display elements, wherein a first one of the display elements represents the generated likelihood value, and wherein a second one of the display elements is operable by a user to select whether the reported injury should be considered in the adjudication of the insurance claim. The GUI can be output to a requesting one of the client devices 16(1)-16(n) to allow an adjuster user, for example, to obtain an automated indication regarding whether the reported injury is likely a result of the motor vehicle accident and should be considered in an adjudication of the insurance claim.

The insurance claim analysis device 12 may optionally generate a GUI that includes an indication that the reported injury of the occupant does or does not likely result from the motor vehicle accident associated with the insurance claim. In other examples, the likelihood value and/or indication that the reported injury of the occupant does not likely result from the motor vehicle accident associated with the insurance claim can be provided for API consumption by an end user of one of the client devices 16(1-16(n).

In step 314, the insurance claim analysis device 12 may receive, via the GUI, a selection regarding whether the reported injury should be considered in the adjudication of the insurance claim. Referring more specifically to FIG. 5, a screenshot of an exemplary GUI 500 is illustrated. In this example, the GUI 500 includes display elements that represent a portion of the data obtained as described earlier with reference to step 300 of FIG. 3. In particular, the GUI 500 includes injury data such as an injury severity score or an equivalent thereof (e.g., "minor" or "moderate") and associated condition indications, which in this example are ICD codes referred to as "diagnosis code(s)" for an injury treatment reported in an insurance claim associated with a motor vehicle accident.

The GUI 500 further includes an indication regarding whether the reported injuries likely resulted from the associated motor vehicle accident. In particular, the "joint injury right shoulder" and "sprain right shoulder" reported injuries are indicated as unlikely to have been caused by the motor vehicle accident associated with the insurance claim. The indications could have been output on the GUI 500 as described in detail earlier with reference to step 3102 of FIG. 3, for example. Additionally, the GUI 500 in this example includes "Consider" and "Don't Consider" buttons that are configured to receive, and facilitate storage of, a selection regarding whether the associated reported injury should be considered in an adjudication of the insurance claim. Other types of GUIs with other types of information and/or methods of outputting the indications and/or receiving or storing the selections could also be used in other examples.

In step 316, the insurance claim analysis device 12 may automatically facilitate adjudication of the electronic insurance claim based on the generated likelihood value for example by automatically generating a recommendation value based on said value and the Consider/Don't Consider injuries. With this technology, a determination regarding whether an injury reported as part of an insurance claim likely resulted from an associated motor vehicle accident can advantageously be determined based on an automated analysis of insurance claim data, including damaged motor vehicle images. This technology utilizes machine learning models to facilitate improved accuracy, consistency, and efficiency with respect to analyzing images and data associated with insurance claims to automatically recommend inclusion or exclusion of associated reported injuries from claim adjudication consideration. The automated generation and utilization of delta velocity values and injury severity scores mapped to condition indications of this technology is not well-understood, routine, or conventional in the art and facilitates an end-to-end, practical, automated, and improved analysis of insurance claim data.

The disclosed technology enables many use cases. In a first use case, the analysis may be leveraged to steer claims to particular groups of adjusters within a claims management organization. For example, when it is determined that no injuries related to the motor vehicle accident are present, the claim may be steered to the damage group only, thereby relieving the injury group of the burden of evaluating the claim. As another example, when a claims management organization has an injury group with multiple subgroups devoted to different injury severities, the claim may be steered to the appropriate subgroup based on the determined injury severity score.

In another use case, as more information becomes available following an initial analysis, that information may be incorporated into the system to obtain an improved analysis. For example, an initial analysis may include injury data from a first injury report, a first notice of loss, or an insurance claim only. Later, when a medical bill is generated, injury data from the medical bill may be incorporated into the system to obtain an improved analysis.

The disclosed technology also provides many advantages over existing systems. For example, the disclosed technology significantly reduces the time required for processing a claim. This allows the claims management organization to quickly reach out to the claimant to obtain an early settlement. As another example, the disclosed technology reduces the burden on the claims adjusters by reducing the degree of analysis required of them, and by automatically steering claims to the appropriate claim adjusters. This improves the efficiency of the claims management organization.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

Figure 6:
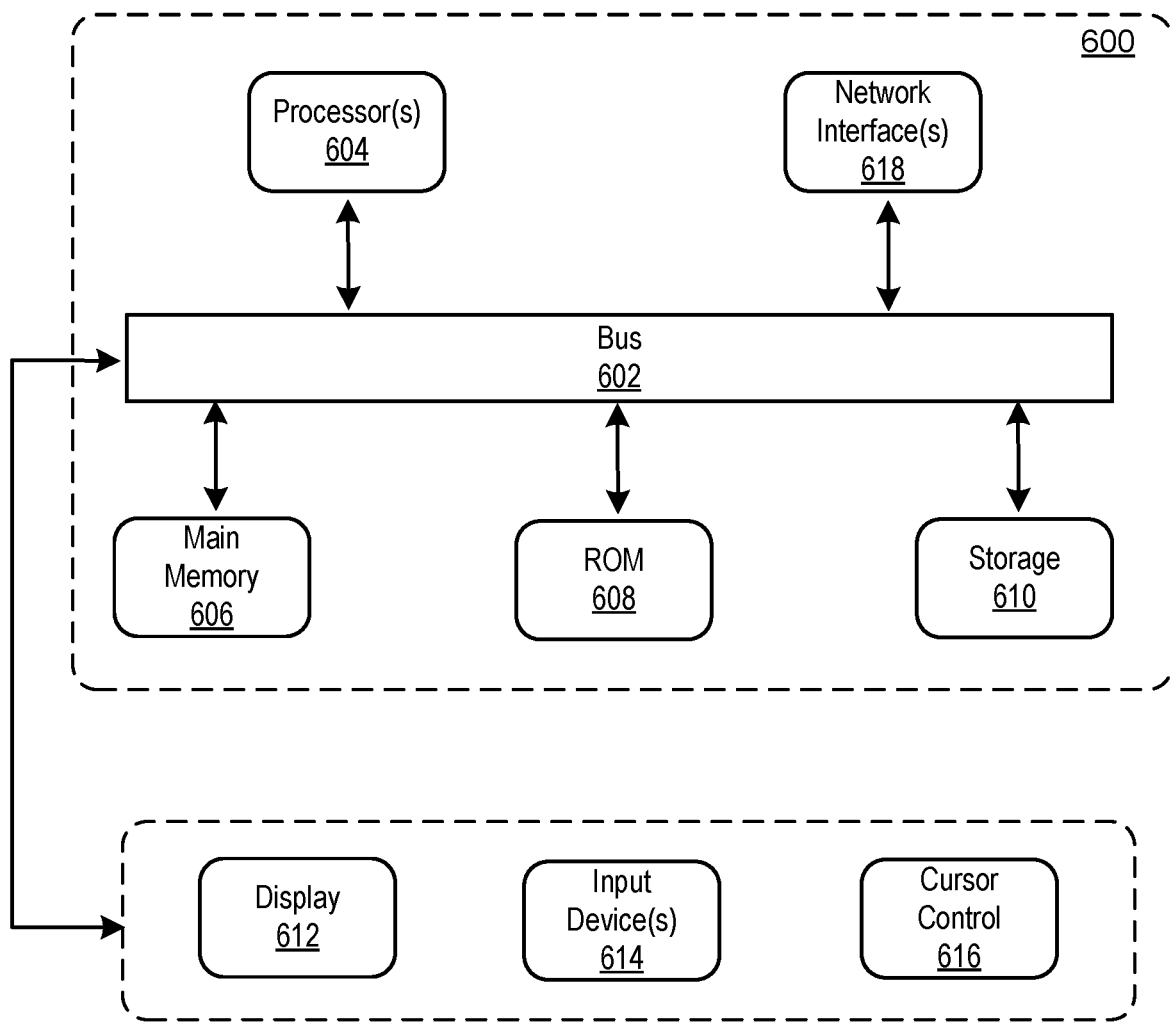
FIG. 6 is an example computing component that may be used to implement various features of embodiments described in the present disclosure.

FIG. 6 depicts a block diagram of an example computer system 600 in which embodiments described herein may be implemented. The computer system 600 includes a bus 602 or other communication mechanism for communicating information, one or more hardware processors 604 coupled with bus 602 for processing information. Hardware processor(s) 604 may be, for example, one or more general purpose microprocessors.

The computer system 600 also includes a main memory 606, such as a random access memory (RAM), cache and/or other dynamic storage devices, coupled to bus 602 for storing information and instructions to be executed by processor 604. Main memory 606 also may be used for storing temporary variables or other intermediate information during execution of instructions to be executed by processor 604. Such instructions, when stored in storage media accessible to processor 604, render computer system 600 into a special-purpose machine that is customized to perform the operations specified in the instructions.

The computer system 600 further includes a read only memory (ROM) 608 or other static storage device coupled to bus 602 for storing static information and instructions for processor 604. A storage device 610, such as a magnetic disk, optical disk, or USB thumb drive (Flash drive), etc., is provided and coupled to bus 602 for storing information and instructions.

The computer system 600 may be coupled via bus 602 to a display 612, such as a liquid crystal display (LCD) (or touch screen), for displaying information to a computer user. An input device 614, including alphanumeric and other keys, is coupled to bus 602 for communicating information and command selections to processor 604. Another type of user input device is cursor control 616, such as a mouse, a trackball, or cursor direction keys for communicating direction information and command selections to processor 604 and for controlling cursor movement on display 612. In some embodiments, the same direction information and command selections as cursor control may be implemented via receiving touches on a touch screen without a cursor.

The computing system 600 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the techniques herein are performed by computer system 600 in response to processor(s) 604 executing one or more sequences of one or more instructions contained in main memory 606. Such instructions may be read into main memory 606 from another storage medium, such as storage device 610. Execution of the sequences of instructions contained in main memory 606 causes processor(s) 604 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 610. Volatile media includes dynamic memory, such as main memory 606. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 602. Transmission media can also take the form of acoustic or light waves, such as those generated during radio-wave and infra-red data communications.

The computer system 600 also includes a communication interface 618 coupled to bus 602. Network interface 618 provides a two-way data communication coupling to one or more network links that are connected to one or more local networks. For example, communication interface 618 may be an integrated services digital network (ISDN) card, cable modem, satellite modem, or a modem to provide a data communication connection to a corresponding type of telephone line. As another example, network interface 618 may be a local area network (LAN) card to provide a data communication connection to a compatible LAN (or a WAN component to communicate with a WAN). Wireless links may also be implemented. In any such implementation, network interface 618 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 618, which carry the digital data to and from computer system 600, are example forms of transmission media.

The computer system 600 can send messages and receive data, including program code, through the network(s), network link and communication interface 618. In the Internet example, a server might transmit a requested code for an application program through the Internet, the ISP, the local network and the communication interface 618.

The received code may be executed by processor 604 as it is received, and/or stored in storage device 610, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 600.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A method for automatically determining injury treatment relation to a motor vehicle accident, the method comprising:

obtaining, by an insurance claim analysis device, a plurality of images of a damaged motor vehicle involved in a motor vehicle accident, vehicle data describing the motor vehicle, occupant data describing an occupant who occupied the motor vehicle during the motor vehicle accident, and injury data from an electronic insurance claim associated with the motor vehicle accident, the injury data specifying an injury to the occupant;

determining, by the insurance claim analysis device, a delta velocity value for the damaged motor vehicle by applying a first machine learning model to the plurality of images of the damaged motor vehicle and the vehicle data, wherein the first machine learning model has been trained using historical sets of images and vehicle data along with delta velocity values obtained from corresponding historical sets of images and vehicle data;

determining, by the insurance claim analysis device, an injury severity score by applying a second machine learning model to the delta velocity value for the damaged motor vehicle, the vehicle data, and the occupant data, wherein the second machine learning model has been trained using historical sets of delta velocity values, vehicle data, and occupant data, along with injury severity scores obtained from corresponding historical sets of delta velocity values, vehicle data, and occupant data;

identifying, by the insurance claim analysis device, a first set of one or more condition indications based on a correlation of the injury severity score with a stored mapping of condition indications to injury severity scores;

comparing, by the insurance claim analysis device, one or more of the condition indications in the first set of condition indications to one or more condition indications in a second set of condition indications in the injury data;

generating, by the insurance claim analysis device, a likelihood value based on the comparing, the likelihood value indicating a likelihood that the injury to the occupant resulted from the motor vehicle accident;

automatically adjudicating, by the insurance claim analysis device, the electronic insurance claim based on the generated likelihood value;

obtaining, by the insurance claim analysis device, further injury data from a medical bill of the occupant;

comparing, by the insurance claim analysis device, one or more of the condition indications in the first set of condition indications to one or more condition indications in a third set of condition indications in the further injury data;

generating, by the insurance claim analysis device, a further likelihood value based on the comparing, the further likelihood value indicating a further likelihood that the injury to the occupant resulted from the motor vehicle accident;

automatically adjudicating, by the insurance claim analysis device, the electronic insurance claim based on the generated further likelihood value;

providing the adjudicated electronic insurance claim to a claims adjusters;

retraining the first machine learning model using the delta velocity value determined using the first machine learning model; and retraining the second machine learning model using the injury severity score determined using the second machine learning model.

2. The method of claim 1, further comprising:

providing, by the insurance claim analysis device, a graphical user interface (GUI) comprising a plurality of display elements, wherein a first one of the display elements represents the generated likelihood value, and wherein a second one of the display elements is operable by a user to select whether the injury should be considered in the adjudication of the insurance claim; and receiving, by the insurance claim analysis device and via the GUI, a selection regarding whether the injury should be considered in the adjudication of the insurance claim.

3. The method of claim 1, wherein the condition indications comprise International Statistical Classification of Diseases and Related Health Problems (ICD) codes and the injury severity score comprises an Abbreviated Injury Scale (AIS) score.

4. The method of claim 1, wherein the vehicle data comprises one or more of a type of the motor vehicle, an age of the motor vehicle, a size of the motor vehicle, a weight of the motor vehicle, an area of impact on the motor vehicle, a damage extent, one or more crush measurements, or whether the motor vehicle was drivable subsequent to the motor vehicle accident.

5. The method of claim 1, wherein the occupant data comprises one or more of demographic data regarding the occupant comprising one or more of an occupant age, weight, height, or gender, where the occupant was sitting in the motor vehicle, a point of impact on the motor vehicle, or whether an airbag deployed as a result of the motor vehicle accident.

6. An insurance claim analysis device comprising memory comprising programmed instructions stored thereon and one or more processors configured to execute the stored programmed instructions to preform a method comprising:

obtaining, by an insurance claim analysis device, a plurality of images of a damaged motor vehicle involved in a motor vehicle accident, vehicle data describing the motor vehicle, occupant data describing an occupant who occupied the motor vehicle during the motor vehicle accident, and injury data from an electronic insurance claim associated with the motor vehicle accident, the injury data specifying an injury to the occupant;

determining, by the insurance claim analysis device, a delta velocity value for the damaged motor vehicle by applying a first machine learning model to the plurality of images of the damaged motor vehicle and the vehicle data;

determining, by the insurance claim analysis device, an injury severity score by applying a second machine learning model to the delta velocity value for the damaged motor vehicle, the vehicle data, and the occupant data;

identifying, by the insurance claim analysis device, a first set of one or more condition indications based on a correlation of the injury severity score with a stored mapping of condition indications to injury severity scores;

comparing, by the insurance claim analysis device, one or more of the condition indications in the first set of condition indications to one or more condition indications in a second set of condition indications in the injury data;

generating, by the insurance claim analysis device, a likelihood value based on the comparing, the likelihood value indicating a likelihood that the injury to the occupant resulted from the motor vehicle accident;

automatically adjudicating, by the insurance claim analysis device, the electronic insurance claim based on the generated likelihood value;

obtaining, by the insurance claim analysis device, further injury data from a medical bill of the occupant;

comparing, by the insurance claim analysis device, one or more of the condition indications in the first set of condition indications to one or more condition indications in a third set of condition indications in the further injury data;

generating, by the insurance claim analysis device, a further likelihood value based on the comparing, the further likelihood value indicating a further likelihood that the injury to the occupant resulted from the motor vehicle accident;

automatically adjudicating, by the insurance claim analysis device, the electronic insurance claim based on the generated further likelihood value;

providing the adjudicated electronic insurance claim to a claims adjusters;

retraining the first machine learning model using the delta velocity value determined using the first machine learning model; and retraining the second machine learning model using the injury severity score determined using the second machine learning model.

7. The insurance claim analysis device of claim 6, the method further comprising:

providing, by the insurance claim analysis device, a graphical user interface (GUI) comprising a plurality of display elements, wherein a first one of the display elements represents the generated likelihood value, and wherein a second one of the display elements is operable by a user to select whether the injury should be considered in the adjudication of the insurance claim; and receiving, by the insurance claim analysis device and via the GUI, a selection regarding whether the injury should be considered in the adjudication of the insurance claim.

8. The insurance claim analysis device of claim 6, wherein the condition indications comprise International Statistical Classification of Diseases and Related Health Problems (ICD) codes and the injury severity score comprises an Abbreviated Injury Scale (AIS) score.

9. The insurance claim analysis device of claim 6, wherein the vehicle data comprises one or more of a type of the motor vehicle, an age of the motor vehicle, a size of the motor vehicle, a weight of the motor vehicle, an area of impact on the motor vehicle, a damage extent, one or more crush measurements, or whether the motor vehicle was drivable subsequent to the motor vehicle accident.

10. The insurance claim analysis device of claim 6, wherein the occupant data comprises one or more of demographic data regarding the occupant comprising one or more of an occupant age, weight, height, or gender, where the occupant was sitting in the motor vehicle, a point of impact on the motor vehicle, or whether an airbag deployed as a result of the motor vehicle accident.

11. A non-transitory machine readable medium having stored thereon instructions for automatically determining injury treatment relation to a motor vehicle accident comprising executable code that, when executed by one or more processors, causes the processors to perform a method comprising:

obtaining, by an insurance claim analysis device, a plurality of images of a damaged motor vehicle involved in a motor vehicle accident, vehicle data describing the motor vehicle, occupant data describing an occupant who occupied the motor vehicle during the motor vehicle accident, and injury data from an electronic insurance claim associated with the motor vehicle accident, the injury data specifying an injury to the occupant;

determining, by the insurance claim analysis device, a delta velocity value for the damaged motor vehicle by applying a first machine learning model to the plurality of images of the damaged motor vehicle and the vehicle data;

determining, by the insurance claim analysis device, an injury severity score by applying a second machine learning model to the delta velocity value for the damaged motor vehicle, the vehicle data, and the occupant data;

identifying, by the insurance claim analysis device, a first set of one or more condition indications based on a correlation of the injury severity score with a stored mapping of condition indications to injury severity scores;

comparing, by the insurance claim analysis device, one or more of the condition indications in the first set of condition indications to one or more condition indications in a second set of condition indications in the injury data;

generating, by the insurance claim analysis device, a likelihood value based on the comparing, the likelihood value indicating a likelihood that the injury to the occupant resulted from the motor vehicle accident;

automatically adjudicating, by the insurance claim analysis device, the electronic insurance claim based on the generated likelihood value;

obtaining, by the insurance claim analysis device, further injury data from a medical bill of the occupant;

comparing, by the insurance claim analysis device, one or more of the condition indications in the first set of condition indications to one or more condition indications in a third set of condition indications in the further injury data;

generating, by the insurance claim analysis device, a further likelihood value based on the comparing, the further likelihood value indicating a further likelihood that the injury to the occupant resulted from the motor vehicle accident;

automatically adjudicating, by the insurance claim analysis device, the electronic insurance claim based on the generated further likelihood value;

providing the adjudicated electronic insurance claim to a claims adjusters;

retraining the first machine learning model using the delta velocity value determined using the first machine learning model; and retraining the second machine learning model using the injury severity score determined using the second machine learning model.

12. The non-transitory machine readable medium of claim 11, the method further comprising:

providing, by the insurance claim analysis device, a graphical user interface (GUI) comprising a plurality of display elements, wherein a first one of the display elements represents the generated likelihood value, and wherein a second one of the display elements is operable by a user to select whether the injury should be considered in the adjudication of the insurance claim; and receiving, by the insurance claim analysis device and via the GUI, a selection regarding whether the injury should be considered in the adjudication of the insurance claim.

13. The non-transitory machine readable medium of claim 11, wherein the condition indications comprise International Statistical Classification of Diseases and Related Health Problems (ICD) codes and the injury severity score comprises an Abbreviated Injury Scale (AIS) score.

14. The non-transitory machine readable medium of claim 11, wherein:

the vehicle data comprises one or more of a type of the motor vehicle, an age of the motor vehicle, a size of the motor vehicle, a weight of the motor vehicle, an area of impact on the motor vehicle, a damage extent, one or more crush measurements, or whether the motor vehicle was drivable subsequent to the motor vehicle accident; and the occupant data comprises one or more of demographic data regarding the occupant comprising one or more of an occupant age, weight, height, or gender, where the occupant was sitting in the motor vehicle, a point of impact on the motor vehicle, or whether an airbag deployed as a result of the motor vehicle accident.

* * * * *